United States Patent [19]

Mochida et al.

[11] 4,248,965

[45] Feb. 3, 1981

[54] IMMUNOCHEMICAL PROCESS OF MEASURING PHYSIOLOGICALLY ACTIVE SUBSTANCES

[75] Inventors: Ei Mochida, Tokyo; Nobuhisa Ogawa, Omiya; Hiroyuki Shinkai, Kawagoe; Masakatsu Hashimoto, Tokyo, all of Japan

[73] Assignee: Mochida Seiyaku Kabushiki Kaisha, Tokyo, Japan

[21] Appl. No.: 838,947

[22] Filed: Oct. 3, 1977

[30] Foreign Application Priority Data

Oct. 7, 1976 [JP] Japan ................................ 51-120621
Oct. 7, 1976 [JP] Japan ................................ 51-120622

[51] Int. Cl.² ............................................ G01N 33/54
[52] U.S. Cl. ..................................... 435/7; 23/230 B; 424/1; 424/12
[58] Field of Search .............. 195/103.5 A; 23/230 B; 424/12, 1; 435/7

[56] References Cited

U.S. PATENT DOCUMENTS

| | | | |
|---|---|---|---|
| 3,654,090 | 4/1972 | Schuurs et al. | 195/103.5 A |
| 3,791,932 | 2/1974 | Schuurs et al. | 195/103.5 A |
| 3,850,752 | 11/1974 | Schuurs et al. | 195/103.5 A |
| 4,016,043 | 4/1977 | Schuurs et al. | 195/103.5 A |
| 4,067,959 | 1/1978 | Bolz | 424/1 |

*Primary Examiner*—Lionel M. Shapiro
*Attorney, Agent, or Firm*—Brisebois & Kruger

[57] ABSTRACT

Immunochemical measurement by either (1) the reaction of the measurement substance with the insolubilized substance and then the reaction of the reaction product of the first procedure with the labeled substance or (2) the reaction of the measurement substance with the labelled substance and then the reaction of the resulting reaction product with the insolubilized substance, or (3) the simultaneous reaction of the three substances.

12 Claims, 9 Drawing Figures

IMMUNOCHEMICAL PROCESS OF MEASURING PHYSIOLOGICALLY ACTIVE SUBSTANCES

BACKGROUND OF THE INVENTION

Substances such as insulin, chorionic gonadotropin, growth hormone, α-fetoprotein and immunoglobulin having antigenicity hereinafter referred to antigenic substances bind to the antibodies against these substances very specifically and very sensitively. Taking advantage of these features, numerous processes have been developed to measure the antigenic substances or their antibodies and many immunochemical measuring processes are already in practical use. To mention some examples, there are; immunodiffusion methods, in which the antigen and the antibody are caused to react with each other in agar gel; agglutination reaction and agglutination inhibition reaction methods, in which blood cells or fine particles like polystyrene latex are utilized as carrier of antigen or antibody; radioimmunoassay (RIA), in which radiosotopes are employed to label the antigen or antibody; enzyme immunoassay (EIA), in which enzymes are employed for the same purpose; and fluoroescence immunoassay, in which fluorescent materials are employed for the same purpose.

Meanwhile there is a competitive protein binding assay, in which a receptor protein or binding protein, i.e., a protein which specifically binds to the substance to be measured is utilized instead of the antibody in the immunochemical process.

These processes with respective characters are finding wide applications. Among others, RIA and EIA, which are far superior in the sensitivity of measurement and quantitative precision, are widely used, the substances measurable by them ranging from high molecular substances such as protein hormones, virus, immunoglobulins to low molecular ones such as peptides, steroids, synthetic medicines.

The principle, which is common to RIA and EIA, is characterized by two methods; competitive method and sandwich method.

The present specification concerns a case of the antigen as the substance to be measured and the antibody as the substance specifically bindable with said antigen. Not being confined to this case alone, however, the present invention is applicable equally to a case of the antibody as the substances to be measured and of the antigen as the bindable substance with said antibody; to an antigen-antibody system; and even to a physiologically active substance-receptor protein system.

Next, referring to a drawing, the competitive method and the sandwich method in RIA and in EIA are to be described.

As schematically illustrated in FIG. 1, the competitive method works such that an unknown amount of unlabeled antigen 1 and a given amount of labeled antigen 2 which is labeled by labeling agent are caused to react competitively with a given amount of the corresponding antibody 3. In this case, the unlabled antigen 1 and the labeled antigen 2 bind to the antibody 3 in proportion to their respective amounts and thereby the amount of the labeled antigen 2 to bind to the antibody 3 is reversely proportional to the amount of the unlabeled antigen 1. Next, by appropriate way the bound labeled antigen 2a and the free labeled antigen 2 are separated and the activity of the labeling agent in either of the two is measured. In the meantime a dilution series of reference substance, whose concentration is known, is prepared and in the same way described above the activity of labeling agent in each dilution is measured. A standard curve obtained by plotting the measured activities is utilized for determining the amount of the substance to be measured.

In the competitive method, the antigen is measured by causing the antigen to be measured and the labeled antigen to compete one with another for binding to the antibody. If the antibody used is one insolubilized, the antigen can be measured in the same way; moreover, the antibody too can be measured by causing the antibody to be measured and the insolubilized antibody to compete one with another for binding to the labeled antigen. U.S. Pat. Nos. 3,654,090 and 3,850,752 disclose the processes based on this principle. In these processes, the labeled substance directly binds to the insolubilized antibody, and this binding is competed by the binding of the substance to be measured to the insolubilized antibody and/or to labeled substance. Thus the amount of the labeled substance to bind to the insolubilized antibody is in reverse proportion to the amount of the substance to be measured.

Next the sandwich method works, as schematically illustrated in FIG. 2, such that an unknown amount of unlabeled antigen 1 to be measured is caused to react with the insolubilized antibody 4, i.e., an antibody to the antigen which has been insolubilized. Both come to bind to each other, yielding an antigen-body complex 5 (the first reaction). The complex 5 is separated from the reaction mixture and caused to react with a given amount of the labeled antibody 6 in which an antibody to antigen to be measured is bound to a labelling agent (the second reaction). The labeled antibody 6 binds to said complex 5, but a part of it which exceeds the bindability to the insoluble complex 5 remains in free state in the solution without binding to the insoluble complex 5. Next the bound labeled antibody 6a and the free labeled antibody 6 are separated and the activity of labeling agent in either of them is measured. In the meantime a dilution series of reference substance, whose concentration is known, is prepared and in the same way described above the activity of labeling agent in each dilution is measured. A standard curve obtained by plotting the measured activities is utilized for determining the amount of the substance to be measured.

In the sandwich method, since the labeled substance does not directly bind to the insolubilized antibody but does so through the substance to be measured, the amount of the labeled substance to bind to the insolubilized antibody will be proportional to the amount of the substance to be measured.

U.S. Pat. No. 3,791,932 discloses a process based on this principle.

Whereas in the competitive method a change in the activity of the labeling agent corresponding to increase or decrease of the amount of the antigen to be measured is little and accordingly with a mild slope of the standard curve the sensitivity of measurement is relatively low, in the sandwich method a change in the amount of the antigen to be measured directly corresponds to increase or decrease the activity of the labeling agent and accordingly with a steep slope of the standard curve the sensitivity of measurement is high. In the conventional sandwich method, however, in which after the first reaction between the antigen to be measured and the insolubilized antibody the antigen-antibody complex yielded has to be separated from the reaction mixture, and accordingly the upper limit of measurable amount of antigen is $10^2$–$10^3$ times the lower limit. Meanwhile, the upper limit of the amount of antigen to be measured may often amount to $10^5$–$10^6$ times the lower limit. For instance the blood level of α-fetoprotein is in normal humans less than $1 \times 10^1$ ng/ml, but in a patient with primary hepatoma it may reach even $1 \times 10^6$ ng/ml; in the latter case the specimens at several levels of dilution have to be prepared so that they can be made measurable by the process, whereby repeated dilution is likely to lower the precision of measurement.

SUMMARY OF THE INVENTION

The principal object of present invention is to provide an accurate process of measuring, over a wide range of concentration, a great variety of physiologically active substances which are present in the human body fluid and excretion.

Another object of the present invention is to provide the reagent for measuring physiologically active substances with the principle based on said process.

REFERENCE TO THE DRAWINGS

DETAILED EXPLANATION OF THE INVENTION

The present invention, which represents a combination of the sandwich method and the competitive method, provides an immunochemical measuring process in which after the reaction between the antigen to be measured and the insolubilized antibody to said antigen, the antigen-antibody complex, without being separated from the reaction mixture, is caused to react continuously with the labeled antibody.

Figure 1:
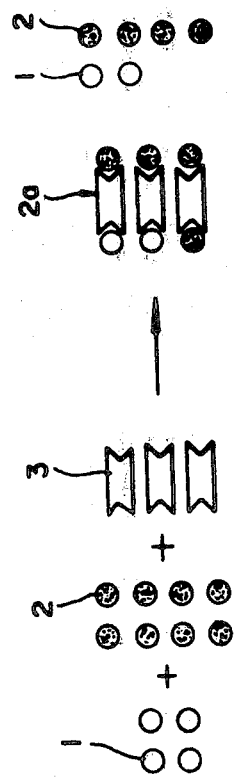
FIG. 1 is a pattern illustrating the principle of the competitive method.
Figure 2:
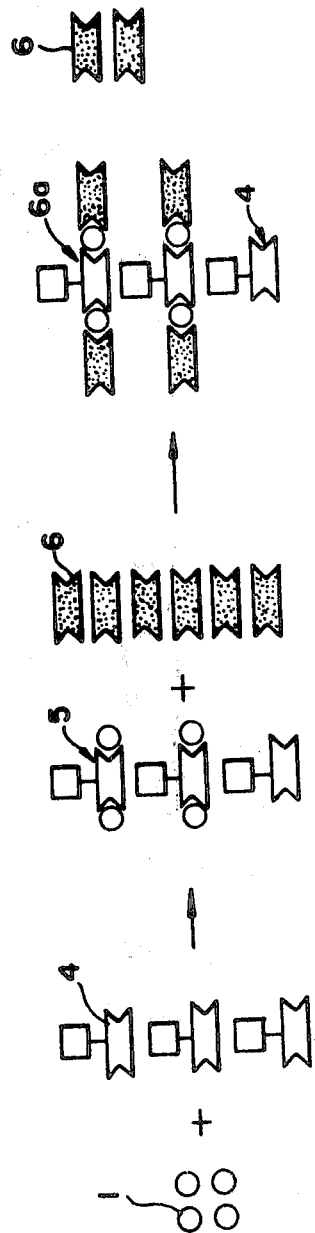
FIG. 2 is a pattern illustrating the principle of the sandwich method.
Figure 3:
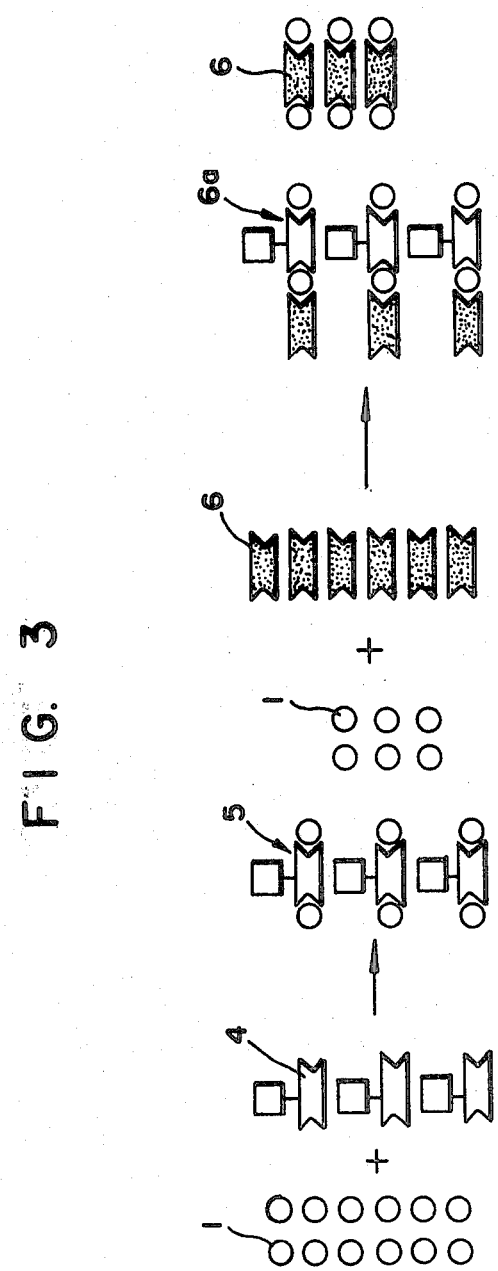
FIG. 3 is a pattern illustrating the principle of the measuring process according to the present invention.

Referring to FIGS. 2 and 3, the principle of the process according to the present invention is to be described.

First an unknown amount of the antigen 1 to be measured and a given amount of the insolubilized antibody 4 to said antigen are to be caused to react one with another. Thereby if the amount of said antigen 1 is smaller than that of said insolubilized antibody 4, the unknown amount of said antigen 1 should be measured in accordance with the principle of the sandwich method illustrated in FIG. 2 (without separating the antigen-antibody complex from the reaction mixture).

Next if the amount of said antigen 1 is larger than that of said insolubilized antibody 4, as shown in FIG. 3, a given amount of a labeled antibody 6 is caused to react with the mixture of them in the presence of a free antigen 1 in addition to the antigen-antibody complex 5 and in consequence a competition to bind to the labeled antibdy 6 takes place between the antigen-antibody complex 5 and said free antigen 1. Thereby the more the free antigen 1, the less becomes the amount of the labeled antibody 6 which binds to the antigen-antibody complex 5. Thus the activity of the labeling agent which has bound to the antigen-antibody complex will decrease in reverse proportion to an increase in the amount of the antigen.

Namely in the present invention the appropriate principle can be selected depending on the quantitative relation between antigen and antibody. When the amount of the antigen to be measured is smaller than that of the insolubilized antibody in the reaction system, the principle of the sandwich method works; and when vice versa, the principle of the competitive method does. In a case of measuring the activity of the labeling agent which has bound to the antigen-antibody complex, the standard curve makes an inverted V-letter with an increase in the amount of the antigen to be measured; and in the case of measuring the activity of the labeling agent which has not bound to it, the standard curve makes a V-letter with an increase in the amount of the antigen to be measured.

In the present invention unlike in the U.S. Pat. No. 3,654,090, even when working on the principle of the competitive method the labeled substance binds to the insolubilized antibody through the substance to be measured just as in the sandwich method. Thus with selection of the binding mode it is possible to combine the sandwich method with the competitive method and accordingly to enlarge the range of the measurable amount of the substance to be measured.

Moreover in the present invention which is characterized by no separation of the antigen-antibody complex from the reaction mixture it is possible to reverse the order of the first and second reactions or to execute them simultaneously. Namely, the antigen to be measured and the labeled antibody are caused to react together to form an antigen-antibody complex in the first reaction; and without separation of said complex from the reaction mixture said complex is continuously caused to react with the insolubilized antibody in the second reaction; or the first and the second reaction take place by causing the antigen to be measured to react with a preliminarily obtained mixture of the labeled antibody and the insolubilized antibody. Next the complex of labeled antibody and the antigen to be measured and the insolubilized antibody is separated from the reaction mixture and then the activity of the labeling agent in said complex or that of the labeling agent remaining in the reaction mixture is measured.

According to this process, the reaction between the antigen to be measured and the labeled antibody takes place in liquid-liquid phase. Therefore with the reaction fully promoted, a greater amount of the labeled antibody binds to the antigen, resulting in a steep enough slope of the standard curve and in an increased sensitivity of measurement.

The separation of the labeled antibody having bound with the antigen-antibody complex from the labeled antibody having not bound therewith is usually conducted centrifugally, as shown in the examples set forth below. Since the above-mentioned antigen-antibody complex is a bound product of the insolubilized antibody and the antigen to be measured, the antigen-antibody complex per se is insoluble. Therefore, the insolubilized antibody and the antigen to be measured can be separated readily by centrifugalizing the reaction mixture.

As examples of carriers to insolubilize antibody, polysaccharides (for example, cellulose, agarose, dextran, etc.) or plastics (for example, polystyrene, polyethylene, polyacetate, polyvinyl chloride, polypropylene, acrylonitrile-butadiene-stylene-copolymer, etc.) are listed.

As the labeling agent the following are available; redioisotopes (for instance, $^{125}I$, $^{131}I$, $^{3}H$, $^{14}C$); enzymes (for instance, horseradish peroxidase, alkaline phosphatase, $\beta$-D-galactosidase, glucose oxidase, glucoamylase); and fluorescent materials (for instance, fluorescein isothiocyanate, rhodamine). They have respective characters, but considering the sensitivity, the precision and the convenience of measurement, enzymes are found the most advantageous.

The present invention is executed usually as follows.

An antigen solution with an appropriate concentration is added to a suspension of the insolubilized antibody for reaction. To the reaction mixture is added a solution of the labeled antibody and after the reaction the solid phase is centrifugally separated. Following a well washing, the activity of the labeling agent contained is measured. When for instance the labeling agent is an enzyme, the well-washed solid phase is added to the solution of substrate against said enzyme and after the reaction the activity of the enzyme is measured. Plotting the measured value over the standard curve obtained by using a reference material with known concentration, the amount of antigen in the test solution is determined.

In the execution of measurement, the conditions such as volume of test solution, the concentration and the volume of the reagent to be used and the reaction temperature and time, which depend on the kind of substance to be measured, the titer of antibody, the kind and activity of the labeling agent, should be experimentally optimized for each measurement.

The activity measurement of the labeling agent may be done either in the solid phase or liquid phase after centrifugal separation. In the present invention, in which after the reaction between the test solution and the insolubilized antibody the antigen-antibody complex is not separated from the reaction mixture, the activity measurement of the liquid phase is likely to be hindered by presence of impurities in the test solution. Therefore when the labeling agent is an enzyme, it would be advantageous to measure the activity of solid phase.

The measurable substances by the present invention include high molecular substances, for instance, human chorionic gonadotropin, growth hormone, insulin, glucagon, adrenocorticotropic hormone, thyroid stimulating hormone, immunoglobulin E, $\alpha$-fetoprotein, hepatitis B antigen, human placental lactogen and their antibody; and low molecular ones, for instance, steroids such as testosterone, estriol, progesterone, corticosterone, aldosterone; thyroid hormones such as thyroxine, triiodothyronin; physiologically active peptides such as bradykinin, gastrin, angiotensin, thyroid hormone-releasing hormone, luteinizing hormone-releasing hormone; physiologically active amines such as epinephrine, norepinephrine, histamine, serotonin; prostaglandin.

The present invention possesses the following advantages over the conventional measuring process.

The present invention, as mentioned above, is a combination of the sandwich principle and the competitive principle and accordingly it is applicable over a wide range of concentration of substance to be measured. This means that when the amount of substance to be measured present in the test solution is unpredictable because of wide range of the amount of the substance to be measured, there is no need of preparing several dilutions to fit into the conventional measurable range; the operation is simplified; there is little error due to dilution and the precision of measurement can be improved. Whereas in the conventional sandwich method the separation of the reaction product has to be done two times, in the present invention only one time of separation suffices, thereby simplifying the operation, decreasing a loss of the sample through the operation and improving the precision of measurement.

Further, in the present invention, in which after reaction between antigen and antibody the reaction is allowed to go on without separating the antigen which has not bound to the antibody, even the antigen which has not fully reacted with the antibody in short time can well bind to the antibody. Thus with the amount of the antigen to bind to the antibody increased, the process according to the present invention can have the sensitivity of measurement which is improved over that of conventional processes.

Furthermore, in the present invention, if the antigen to be measured and the labeled antibody are first caused to react together as the first reaction, the reaction between the antigen to be measured and the labeled antibody will take place in liquid-liquid phase. Thus with the reaction fully promoted, more of the labeled antibody can bind to the antigen to be measured, resulting in the slope of the standard curve becoming steep enough and the sensitivity of measurement being improved.

The present invention is illustrated by the following examples.

Example 1—Measurement of $\alpha$-fetoprotein (a) Preparation of Standard $\alpha$-Fetoprotein Solutions $\alpha$-fetoprotein (AFP) extracted from abdominal ascites of patient with primary hepatoma and purified by S. Nishi and others' method (S. Nishi, Cancer Res., 30, 2507–2513 (1970)) was dissolved in PBS (Phosphate buffered saline) containing 0.5% Tween 20 and 1% BSA (bovine serum albumin) to concentrations of $10^1$, $10^2$, $10^3$, $10^4$, $10^5$, $10^6$, and $10^7$ ng/ml.

(b) Preparation of Anti-AFP Antibody

The purified AFP in (a) was dissolved to a concentration of 2 mg/ml in physiological saline and 0.5 ml of the solution was mixed with 0.5 ml of Freund's complete adjuvant and the mixture was injected more than 5 times into a rabbit, and therefrom anti-AFP antiserum was obtained. This antiserum was salted out by sodium sulfate and thus anti-AFP antibody globulin was obtained.

(c) Preparation of Anti-AFP Antibody Coupled Cellulose

Eight g of cellulose powder (Merk chemical) was added to 320 ml of 2.5% cyanogen bromide; adjusted to pH 10~11 with 1 N sodium hydroxide; stirred for two minutes to react; passed through a glass filter; and washed with 0.1 M sodium bicarbonate, producing activated cellulose. The activated cellulose obtained was suspended in 32 ml of 0.1 M sodium bicarbonate. To this suspension was added 8 mg of said anti-AFP antibody and reacted for 22 hours at 4° C. under stirring. After this reaction, the anti-AFP antibody coupled cellulose was washed with 8 M urea 0.2 M glycine mixture (pH 7.0) and suspended to a concentration of 10% in PBS containing 0.5% Tween 20 and 1% BSA.

(d) Preparation of anti-AFP antibody-enzyme conjugate

Five mg of HRP (horseradish peroxidase) was dissolved in 1 ml of 0.3 M sodium bicarbonate; mixed with 0.1 ml of 1% 2.4-dinitrofluorobenzene; and stirred for one hour at room temperature. To the solution obtained was added 1 ml of 0.08 M sodium periodate, followed by stirring for 30 minutes at room temperature; after adding 1.0 ml of 0.16 M ethylene-glycol solution the mixture was stirred for one hour at room temperature. After dialysis overnight against 0.01 M sodium carbonate buffer (pH 9.5), to the dialyzate was added 1.0 ml of anti-AFP antibody solution, i.e., the anti-AFP antibody prepared in (b) was dissolved to a concentration of 5 mg/ml in 0.01 M sodium carbonate buffer (pH 9.5). After the reaction for three hours at room temperature, 5 mg of sodium borohydride was added to the reaction mixture followed by incubation for three more hours at 4° C. After dialysis overnight against PBS (pH 7.2), anti-AFP antibody-HRP conjugate (hereinafter referred to anti-AFP-HRP) was purified through fractionation by Sephadex G-200.

(e) Measurement of AFP

Figure 4:
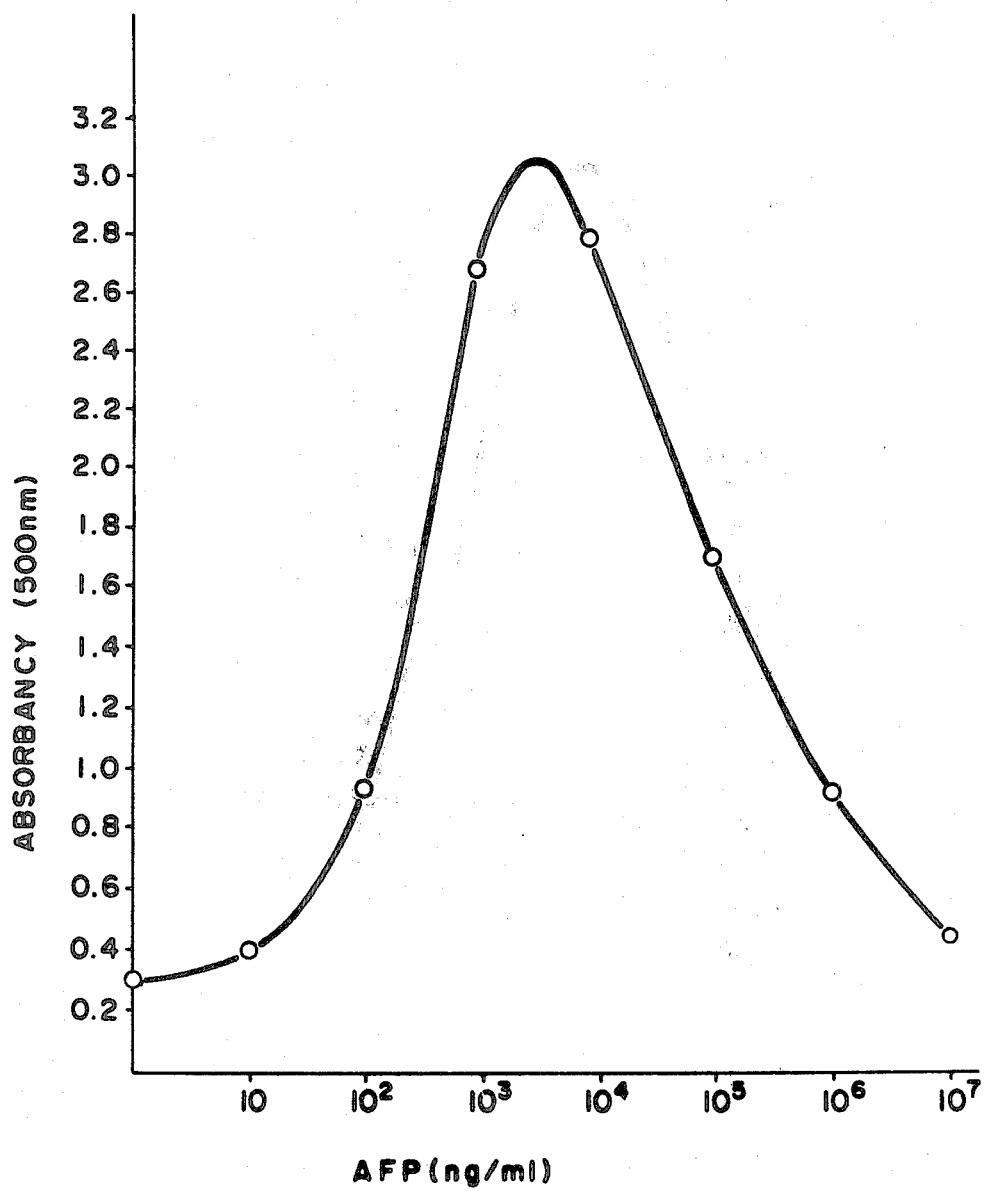
FIG. 4 shows a standard curve for AFP measurement in the Example 1.

In a test tube 0.1 ml of the standard AFP solution of each concentration prepared in (a) was put and to this, 0.4 ml of the anti-AFP antibody coupled cellulose suspension in (c) was added and the suspension was reacted for 60 minutes at room temperature. Following the reaction, 0.1 ml of anti-AFP-HRP obtained in (d) was added to the reaction mixture and was reacted for 120 minutes at room temperature. After the reaction, the solid phase was centrifugally separated; washed two times with a physiological saline containing 0.005% Tween 20; and then to the washed solid phase was added to 3 ml of a substrate solution containing 60 mg/dl of 5-aminosalicylic acid and 1 ml/dl of 0.3% hydrogen peroxide and the enzyme-substrate mixture was kept standing for 60 minutes at room temperature. The reaction was stopped and after centrifugation, the absorbancy of the supernatant fluid was measured at the wave length of 500 nm. The standard curve obtained thereby is illustrated in FIG. 4.

Next, examples of measurement using this curve are described.

Example 2—Measurement of AFP in a healthy person's serum and in a patient's serum.

In accordance with the procedure of Example 1, the amount of AFP in serum was measured on healthy persons, pregnant women and patients with liver disease.

In test tubes 0.05 ml and 0.1 ml of specimens were put and to them was added 0.4 ml of the anti-AFP antibody coupled cellulose obtained in Example 1-(c) and then the tubes were incubated for 60 minutes at room temperature. Subsequently the absorbancy at 500 nm was measured in the same way as in Example 1-(e).

The absorbansy ($OD_{0.05}$) of 0.05 ml of the specimen was compared with that ($OD_{0.1}$) of 0.1 ml of the specimen. In the case of $OD_{0.05} \leq OD_{0.1}$, the rising gradient side of the standard curve, and in the case of $OD_{0.05} > OD_{0.1}$, the falling gradient side of it were used to estimate the AFP concentration in serum, the results being summarized in Table 1.

Table 1

| Case No. | Subject | AFP content |
|---|---|---|
| 1 | Healthy | less than 10 ng/ml |
| 2 | " | " |
| 3 | " | " |
| 4 | Hepatitis | 82 ng/ml |
| 5 | " | less than 10 ng/ml |
| 6 | Liver cirrhosis | 45 ng/ml |
| 7 | Pregnant | 120 ng/ml |
| 8 | " | 53 ng/ml |
| 9 | " | 220 ng/ml |
| 10 | " | 260 ng/ml |
| 11 | Liver cancer | 8180 ng/ml |
| 12 | " | 410 ng/ml |
| 13 | " | 165 ng/ml |
| 14 | " | 6262 ng/ml |

Example 3—Measurement of AFP

Figure 5:
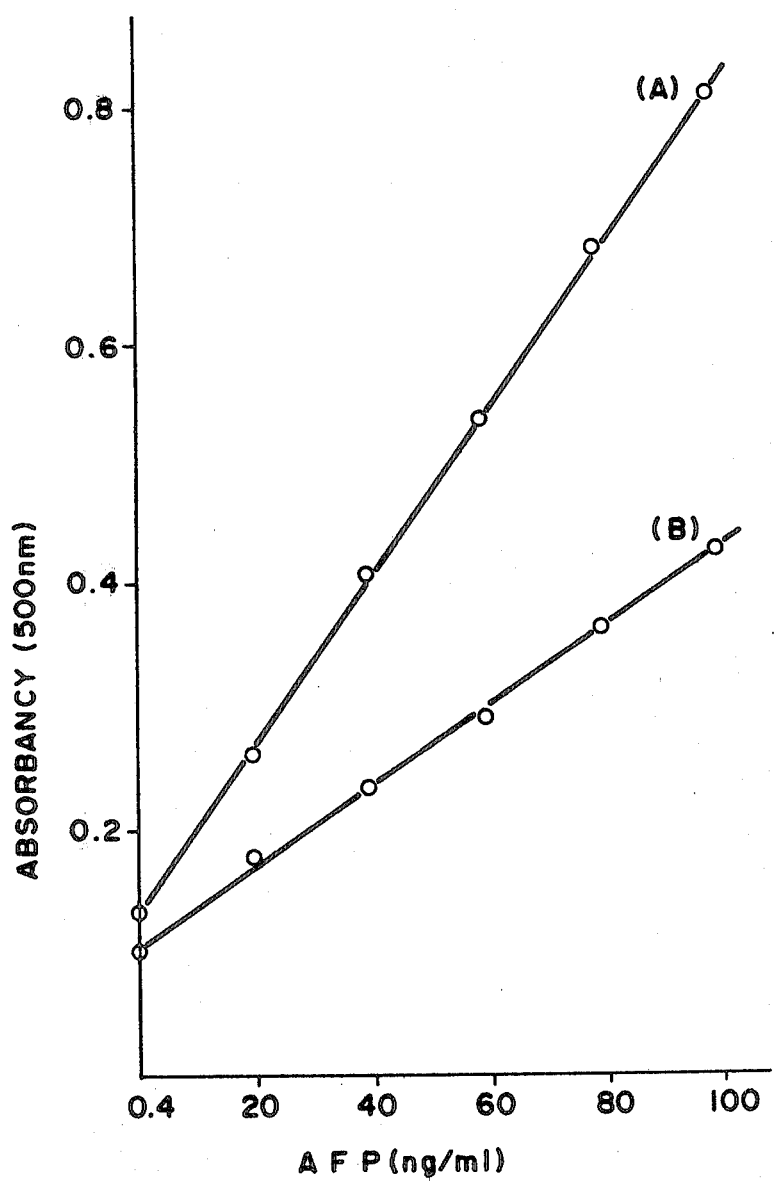
FIG. 5 shows the standard curves for AFP measurement in the Example 3 ([A]) and Comparative case 1 ([B]).

Standard AFP solutions were prepared by dissolving the AFP purified in Example 1-(a) in PBS containing 1% BSA and Tween 20 to concentrations of 100, 80, 60, 40 and 20 ng/ml. In a test tube 0.1 ml of each of these solutions was put and to this was added 0.4 ml of anti-AFP-HRP obtained in Example 1-(d) and the test tubes were inculated for 60 minutes at room temperature. After the incubation, 0.1 ml of the anti-AFP antibody coupled cellulose suspension obtained in Example 1-(c) was added to each reaction mixture and the test tubes were incubated for 120 minutes at room temperature. After the incubation the solid phase was centrifugally separated; washed two times with a physiological saline containing 0.005% Tween 20; and 3 ml of a substrate solution containing 60 mg/dl of 5-aminosalicylic acid and 1 ml/dl of 0.3% hydrogen peroxide was added to the washed solid phase and the test tubes were incubated for 60 minutes at room temperature. Thereafter the absorbancy at 500 nm was measured. The standard curve obtained thereby is illustrated in FIG. 5 [A]. Compared with the one for conventional process, this curve has a slope two times steeper and it can sensitively detect a change in the AFP concentration as a change in the absorbancy.

Comparative Case 1—Measurement of AFP

In test tubes 0.1 ml of each of the AFP standard solutions in Example 3 was put and to these was added 0.4 ml of the anti-AFP antibody coupled cellulose suspension in Example 1-(c) and the tubes were incubated for 60 minutes at room temperature. After the incubation the solid phase was centrifugally separated; washed with a physiological saline containing 0.005% Tween 20; and suspended in PBS containing 0.5% BSA. Then to this suspension was added 0.4 ml of anti-AFP-HRP in Example 1-(d) and the tubes were incubated for 120 minutes at room temperature. After the incubation, the solid phase was centrifugally separated; washed with a physiological saline containing 0.005% Tween 20; and then added to 3 ml of a substrate solution containing 60 mg/dl of 5-aminosalicylic acid and 1 ml/dl of 0.3% hydrogen peroxide and the tubes were incubated for 60 minutes at room temperature. Then the absorbancy at 500 nm was measured, the standard curve thereby being illustrated in FIG. 5 [B].

Example 4—Measurement of AFP (a) Preparation of standard AFP solutions

In accordance with the procedure in Example 1-(a), standard solutions containing a purified AFP in concentrations of 320, 160, 80, 40, 20, 10, 5 and 0 ng/ml were prepared.

(b) Labeling of anti-AFP antibody with radioactive iodine

The anti-AFP antibody in Example 1-(b) was labeled with $^{131}$I. In a small test tube 0.005 ml of 2 mCi Na$^{131}$I was added to 0.025 ml of 0.5 M phosphate buffer. Next, 0.025 ml of anti-AFP antibody solution and 0.02 ml of chloramine T were put and mixed together. In 10 seconds after this, the reaction was stopped by adding 0.1 ml of sodium pyrosulfite solution. Through fractionation by a column of Sephadex G-50, $^{131}$I-labeled anti-AFP antibody was obtained.

(c) Measurement of AFP

Figure 6:
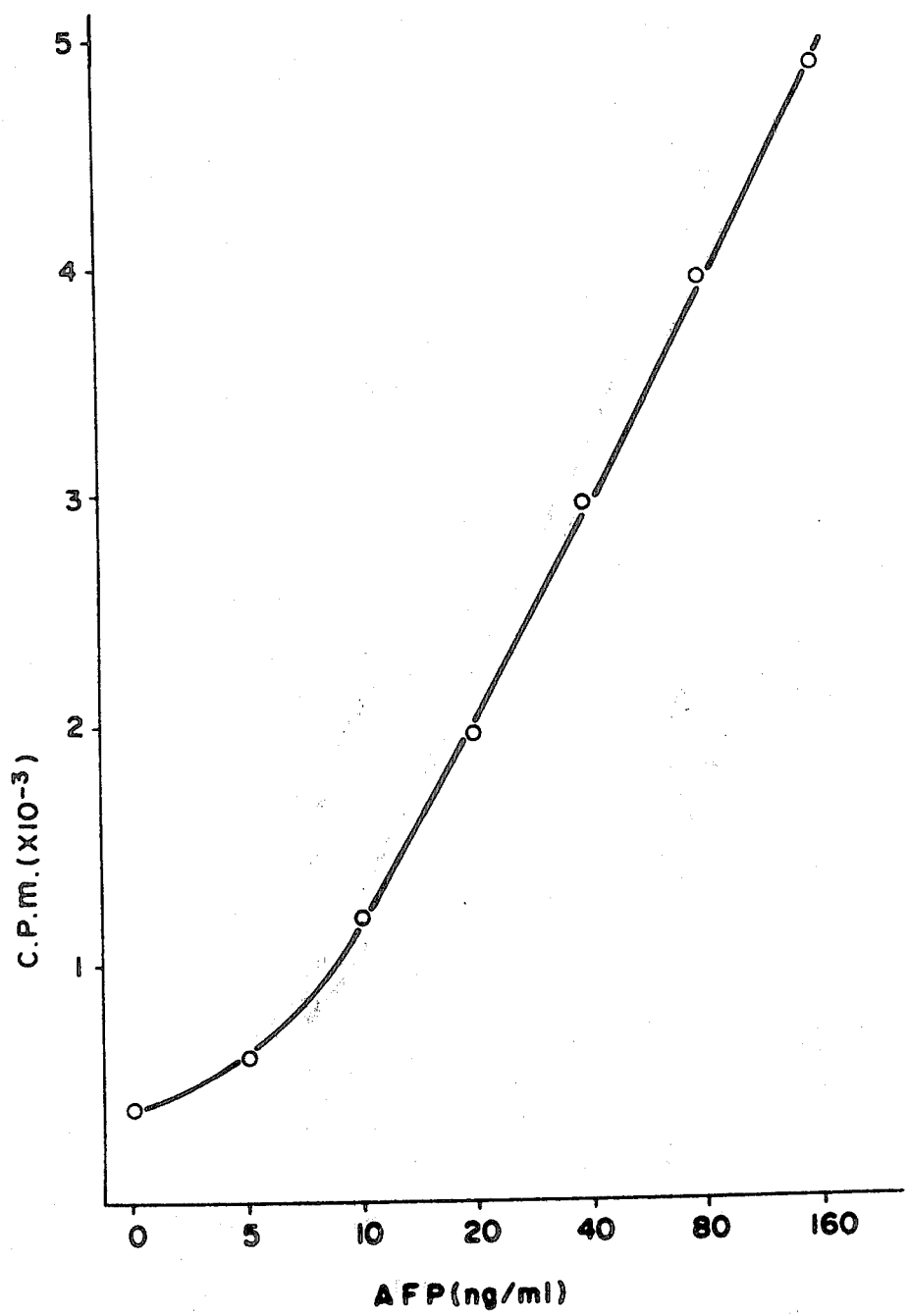
FIG. 6 shows the results of radioactivity measurement in the Example 4.

In a counting test tube 0.1 ml of a standard AFP solution with each concentration prepared in (a) and 0.4 ml of the anti-AFP antibody coupled cellulose suspension obtained in Example 1-(c) were added and the tubes were incubated for 60 minutes at room temperature. Next, 0.1 ml of said $^{131}$I-labeled anti-AFP antibody in (b) was added and the tubes were incubated for 120 minutes at room temperature. Then the solid phase was centrifugally separated; washed with a physiological saline containing 0.005% Tween 20; and then radioactivity was measured, some of the results being given in FIG. 6.

Example 5—Measurement of insulin (a) Preparation of standard insulin solutions

Bovine crystal insulin (Sigma chemical) was dissolved in PBS containing 0.1% BSA to concentration of 160, 80, 40, 20, 10 and 0 μIU/ml.

(b) Preparation of anti-insulin antibody

Bovine crystal insulin suspended in physiological saline; thereafter dissolved by adding 0.1 N hydrochloric acid drop by drop and adjusted to a concentration of 2 mg/ml. The insulin solution was mixed with activated charcoal powder (Wako Pure Chemical) at a rate of 10 mg to 1 ml of said insulin solution, thereby causing insulin to be adsorbed on activated charcoal. The insulin adsorbed charcoal was centrifugally separated. By adding 0.5 ml of physiological saline to 10 mg of this charcoal, the insulin adsorbed activated charcoal suspension was obtained. A guinea pig was injected every other week a mixture of 0.25 ml of this suspension and 0.25 ml of Freund's complete adjuvant and the injection was repeated 10 times. One week after the final injection, the blood was collected from the animal's carotid, thereby producing a guinea pig anti-insulin serum. The antiserum thus obtained was salted out two times with sodium sulfate and the anti-insulin antibody was obtained.

(c) Preparation of anti-insulin antibody-alkaline phosphatase conjugate

Three tenth ml of alkaline phosphatase (Grade I) (Boehringer mannheim) solution (5 mg/ml) was centrifuged and, after removed of the supernatant fluid, it was dissolved in 0.1 ml of the anti-insulin antibody in (b). After dialysis overnight against PBS, it was mixed with 0.01 ml of 4.2% glutaraldehyde and the mixture was incubated for 2 hours at room temperature. Then, the volume of the solution was adjusted to 1 ml with addition of PBS. After dialysis overnight against PBS, dialyzate was fractionated by a Sepharose 6B column chromatography, thereby yielding an anti-insulin antibody-alkaline phosphatase conjugate.

(d) Preparation of anti-insulin antibody-sensitized polyethylene stick

The anti-insulin antibody in (b) was dissolved to a concentration of 10 μg/ml in a glycine buffer (pH 8.2). Into 10 ml of this antibody solution was immersed 100 pieces of polyethylene stick, 3 mm in diameter and 8 mm in length, and the mixture was incubated for three hours at 37° C. The sticks were then washed with physiological saline and immersed in PBS containing 1% normal guinea pig serum. After kept standing this solution overnight at 4° C., anti-insulin antibody-sensitized polyethylene sticks were obtained.

(e) Measurement of insulin

Figure 7:
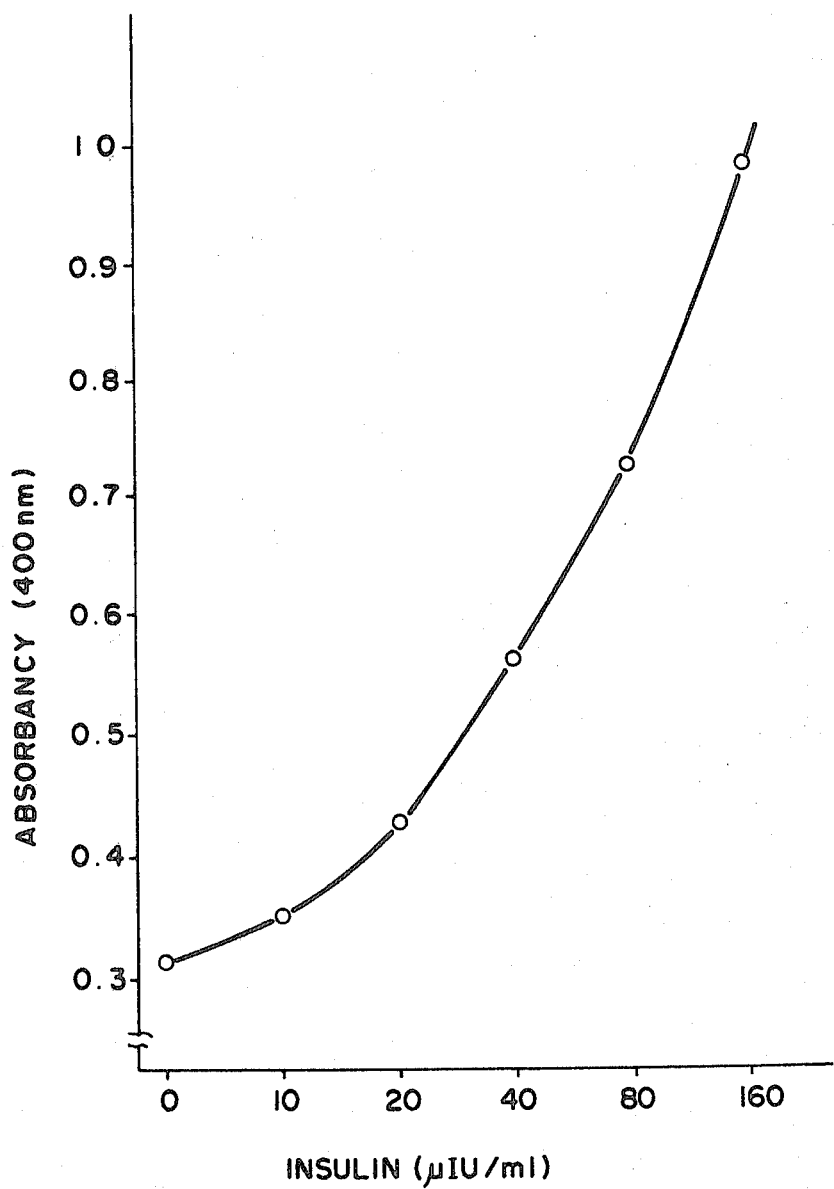
FIG. 7 shows the results of absorbancy measurement in the Example 5.

One tenth ml of standard insulin solution of each concentration obtained in (a) was put in a test tube and was mixed with 0.6 ml of PBS containing 0.5% BSA and 0.5% Tween 20. Then the anti-insulin antibody-sensitized polyethylene sticks prepared in (d) were put, three pieces of stick to each test tube, and the tubes were incubated for one hour at room temperature. Next, 0.1 ml of the anti-insulin antibody-alkaline phosphatase conjugate solution in (c) was added and the tubes were incubated overnight at 4° C. After the incubation, polyethylene sticks, which had been washed with a physiological saline containing 0.005% Tween 20, were put in 3 ml of a substrate solution (p-nitrophenylphosphate 1 mg/ml, magnesium chloride 1 mM: sodium carbonate buffer pH 9.8). After the reaction for one hour at room temperature, 0.3 ml of 1 N NaOH was added and the absorbancy at 400 nm was measured, some of the results being given in FIG. 7.

Example 6—Measurement of insulin (a) Preparation of standard insulin solutions

Bovine crystal insulin was dissolved in PBS (pH 6.4) containing 0.1% BSA to concentrations of $10^4$, $10^3$, 320, 80 and 20 μIU/ml.

(b) Preparation of anti-insulin antibody-HRP conjugate

In accordance with the procedure in Example 1-(d), reaction was made between 5 mg of the anti-insulin antibody prepared in Example 5-(b) and 5 mg of HRP, producing an anti-insulin antibody-HRP conjugate.

(c) Measurement of insulin

Figure 8:
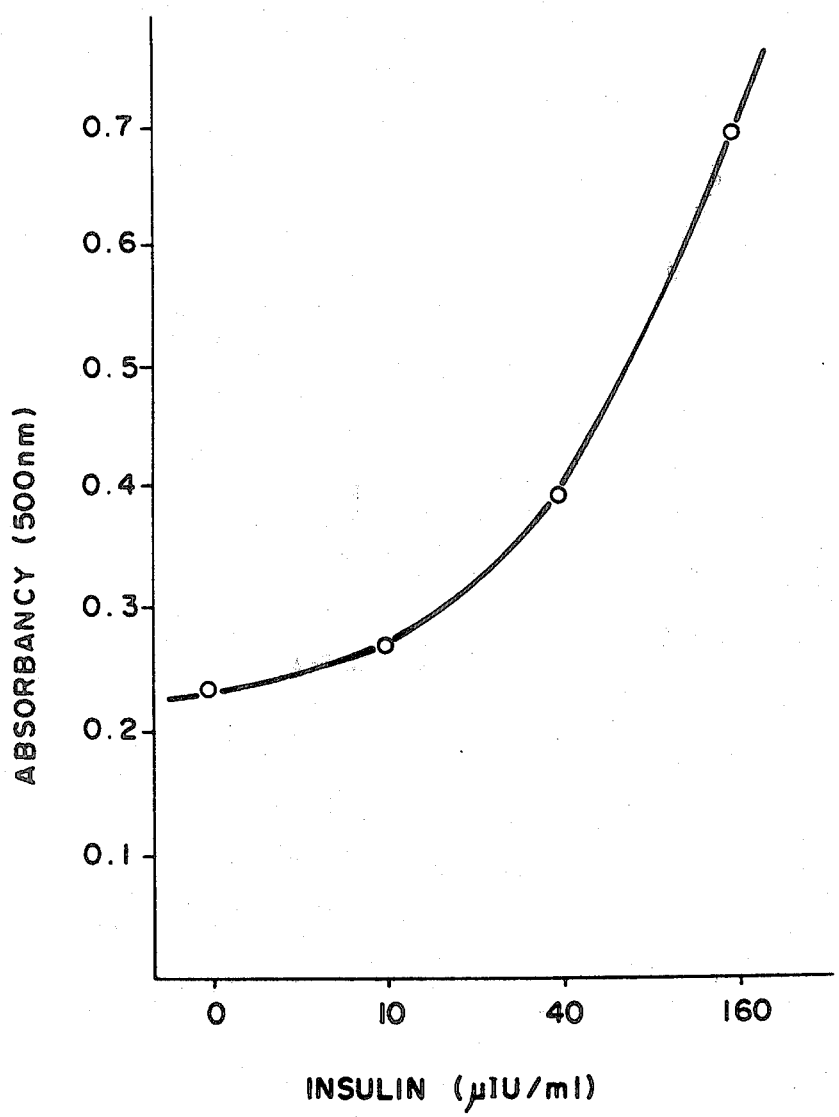
FIG. 8 shows a standard curve for insulin measurement in the Example 6.
Figure 9:
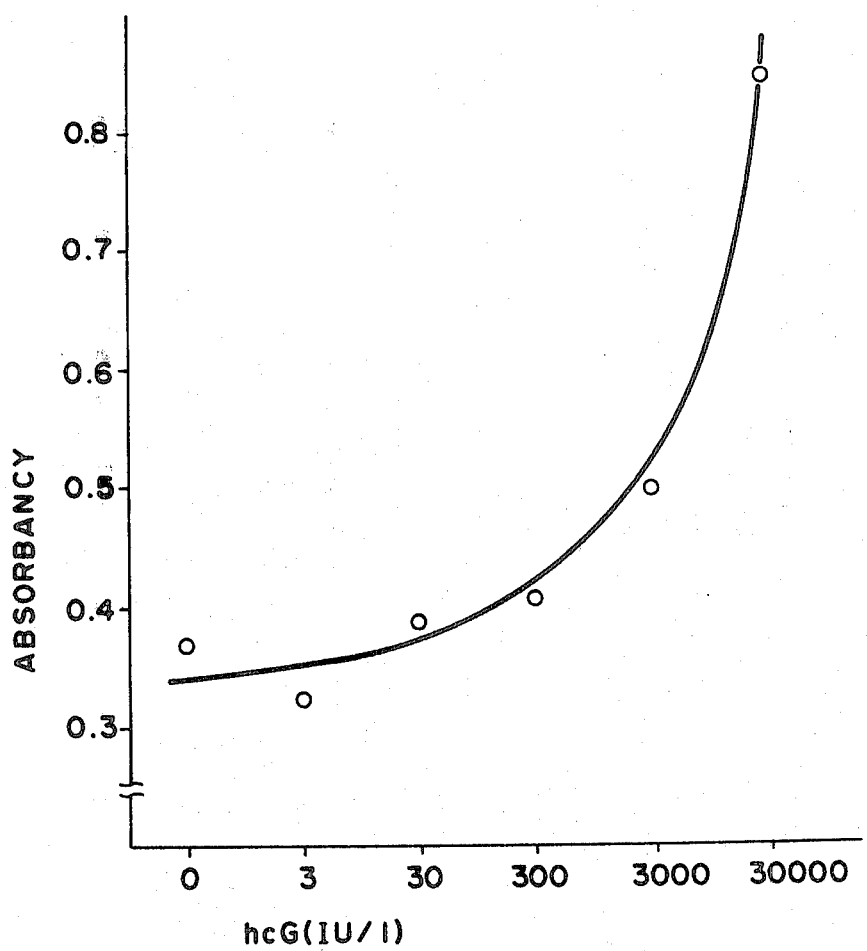
FIG. 9 shows a standard curve for the hCG measurement in the Example 7.

In a test tube 0.1 ml of the standard insulin solution in (a), 0.3 ml of PBS containing 0.5% BSA and 0.5% Tween 20 and 0.1 ml of the anti-insulin antibody-HRP conjugate in (b) were put and the tubes were incubated for one hour at room temperature. Next, 0.5 ml of PBS containing 0.5% BSA and 0.5% Tween 20 and three pieces of anti-insulin antibody-sensitized polyethylene stick in Example 5-(d) were added together and the tubes were incubated overnight at 4° C. After the incubation, these sticks were washed with a physiological saline containing 0.005% Tween 20 and thereto was added 3 ml of a substrate solution (5-amino-salicylic acid 60 μg/dl, 0.3% hydrogen peroxide 1 ml/dl) and the tubes were incubated for 60 minutes at room temperature, after which the absorbancy at 500 nm was measured. The standard curve obtained thereby is illustrated in FIG. 8.

Example 7—Measurement of human chorionic gonadotropin (hCG)

(a) Preparation of standard hCG solutions

Standard hCG specified in Japanese pharmacopoeia was dissolved in PBS containing 0.1% BSA to concentrations of 30,000, 3,000, 300, 30, 3 and 0 IU/l.

(b) Preparation of rat's testis gonadotropin receptor

Tunica albuginea of two testes of a 7~10 weeks old rat was torn off and thereto was added a small amount of PBS. The whole thing was homogenized in a whirling blender for about 30 seconds. The suspension obtained was filtered through a piece of gauze and the filtrate was centrifuged to separate for 10 minutes at 3,000 rpm. The precipitate obtained was resuspended in 10 ml of PBS per one testis.

(c) Preparation of anti-hCG antibody

Commercial hCG was purified by using the anion exchange resin and the gel filtration with Sephadex. Using the product obtained as the antigen, a rabbit was immunized in the same way as in Example 1-(d). Normal human serum and urine were added to the obtained antiserum; the antibody to the components of serum and urine was eliminated through absorption; and after salting out with sodium sulfate, an anti-hCG antibody was obtained.

(d) Preparation of anti-hCG antibody.HRP conjugate

In accordance with the procedure in Example 1-(d), 5 mg of HRP and 5 mg of the anti-hCG antibody and (c) were bound, yielding an anti-hCG antibody-HRP conjugate (e) Measurement of hCG In a test tube, 0.4 ml of PBS containing 0.1% BSA, 0.1 ml of the standard hCG solution in (a) and 0.1 ml of the receptor suspension in (b) were added and the tubes were incubated for 30 minutes at 37° C. Next 0.1 ml of the anti-hCG antibody-HRP conjugate solution was added and the tubes were incubated for 60 minutes at 37° C. After centrifugation for 10 minutes at 3,000 rpm, the supernatant fluid was removed; the precipitated receptor was washed with PBS: and 3 ml of the substrate solution in Example 1-(e) was added and the tubes were incubated for one hour at room temperature.

After the reaction was stopped, centrifugation was done and then the absorbancy of the supernatant fluid was measured, some of the results being given in FIG. 5.

What is claimed is:

1. An immunochemical measuring process comprising the steps of
    (a) mixing and reacting a substance to be measured with a given amount of an insolubilized substance which is obtained by insolubilizing a substance specifically bindable with the substance to be measured,
    (b) without separating the bound product comprising the substance to be measured and the insolubilized substance from the reaction mixture, reacting the reaction product produced in the step (a) with a given amount of a labelled substance which is obtained by labelling a substance specifically bindable with the substance to be measured with a labelling agent,
    (c) separating the reaction product produced in step (b) into an insoluble reaction product which is the solid phase containing the labelled substance which is bound to the insolubilized substance, and a liquid reaction product which is liquid phase, containing the unbound labelled substance, and
    (d) measuring the activity of either the labelled substance bound with said solid phase or the labelled substance existing in the liquid phase.

2. An immunochemical measuring process comprising the steps of
    (a) mixing and reacting a substance to be measured with a given amount of a labelled substance which is obtained by labelling a substance specifically bindable with the substance to be measured with a labelling agent,
    (b) reacting the reaction mixture produced with a given amount of an insolubilized substance which is obtained by insolubilizing a substance specifically bindable with the substance to be measured,
    (c) separating the reaction product produced in the step (b) into an insoluble product (solid phase) and a liquid product (liquid phase), and
    (d) measuring the activity of either the labelled substance bound with the solid phase or the labelled substance existing in the liquid phase.

3. The immunochemical measuring process of claim 2, wherein the steps (a) and (b) are simultaneously carried out.

4. Immunochemical measuring process of claim 1, wherein the substances to be measured include antigenic substances, haptens, antibodies and physiologically active peptides and amines.

5. Immunochemical measuring process of claim 2, wherein the substance to be measured include antigenic substances, haptens, antibodies and physiologically active peptides and amines.

6. Immunochemical measuring process of claim 3, wherein the substances to be measured include antigenic substances, haptens, antibodies and physiologically active peptides and amines.

7. Immunochemical measuring process of claim 1, wherein the insolubilized substance is a bindable substance insolubilized by binding to a carrier.

8. Immunochemical measuring process of claim 2, wherein the insolubilized substance is a bindable substance insolubilized by binding to a carrier.

9. Immunochemical measuring process of claim 3, wherein the insolubilized substance is a bindable substance insolubilized by binding to a carrier.

10. Immunochemical measuring process of claim 1, wherein the labeling agent is radioisotope, enzyme or fluorescent material.

11. Immunochemical measuring process of claim 2, wherein the labeling agent is radioisotope, enzyme or fluorescent material.

12. Immunochemical measuring process of claim 3, wherein the labeling agent is radioisotope, enzyme or fluorescent material.

* * * * *